(12) United States Patent
Gray

(10) Patent No.: US 7,340,294 B2
(45) Date of Patent: Mar. 4, 2008

(54) IMPEDANCE MEASUREMENT APPARATUS FOR ASSESSMENT OF BIOMEDICAL ELECTRODE INTERFACE QUALITY

(75) Inventor: James M. Gray, Fox Point, WI (US)

(73) Assignee: The General Electric Company, Schenactady, NY (US)

( * ) Notice: Subject to any disclaimer, the term of this patent is extended or adjusted under 35 U.S.C. 154(b) by 299 days.

(21) Appl. No.: 11/201,896

(22) Filed: Aug. 11, 2005

(65) Prior Publication Data
US 2007/0038257 A1 Feb. 15, 2007

(51) Int. Cl.
*A61B 5/04* (2006.01)
(52) U.S. Cl. .................................. 600/509; 600/512
(58) Field of Classification Search ................ 600/509, 600/512, 513; 607/68, 71
See application file for complete search history.

(56) References Cited

U.S. PATENT DOCUMENTS

| | | | |
|---|---|---|---|
| 4,506,678 A * | 3/1985 | Russell et al. .............. | 600/536 |
| 4,577,639 A | 3/1986 | Simon et al. | |
| 4,619,265 A | 10/1986 | Morgan | |
| 4,848,335 A | 7/1989 | Manes | |
| 4,919,145 A | 4/1990 | Marriott | |
| 5,020,541 A * | 6/1991 | Marriott ..................... | 600/536 |
| 5,415,164 A | 5/1995 | Faupel | |
| 5,469,857 A | 11/1995 | Laurent et al. | |
| 5,788,644 A | 8/1998 | Donehoo et al. | |
| 5,921,939 A | 7/1999 | Danielsson et al. | |
| 6,516,218 B1 | 2/2003 | Cheng et al. | |
| 6,597,942 B1 * | 7/2003 | Yonce ........................ | 600/509 |

FOREIGN PATENT DOCUMENTS

| | | |
|---|---|---|
| WO | WO-99/11187 | 3/1999 |
| WO | WO-01/76466 | 10/2001 |

OTHER PUBLICATIONS

Medical Instrumentation Application and Design, 3rd Ed., John G. Webster, Editor et al. (1998), p. 198.

* cited by examiner

*Primary Examiner*—Carl Layno
*Assistant Examiner*—Brian T. Gedeon
(74) *Attorney, Agent, or Firm*—Andrus, Sceales, Starke & Sawall, LLP

(57) ABSTRACT

Apparatus for assessing the electrical properties of patient-electrode interfaces has a carrier signal source injecting two carrier signals comprising an AC signal with a DC offset to the electrodes. The carrier signals are out of phase. The outputs from the electrodes are formed into electrocardiographic lead signals in a pre-amplifier circuit. Signal processing circuit is coupled to the pre-amplifier circuit and provides a first signal comprising the AC carrier signal contained in an ECG lead signal and a second signal containing a DC offset signal. The first and second signals are provided to a microprocessor to obtain an output indicative of the electrical properties of electrode interfaces for the ECG lead signal.

20 Claims, 2 Drawing Sheets

IMPEDANCE MEASUREMENT APPARATUS FOR ASSESSMENT OF BIOMEDICAL ELECTRODE INTERFACE QUALITY

FIELD OF THE INVENTION

This invention relates to the evaluation of the electrical characteristics or "quality" of the connection of one or more biomedical electrodes to a patient.

BACKGROUND OF THE INVENTION

The collection of biopotential signals, such as electrocardiographic (ECG), electromyographic (EMG), and electroencephalographic (EEG) signals, is commonly used in minimally invasive techniques for obtaining diagnostic and patient monitoring data. These techniques are performed by placing a plurality of biomedical electrodes in electrical contact with the patient's skin. A patient connection system includes the plurality of electrodes, arranged in different standard configurations depending on the specific biopotential signals to be collected, and lead wires attached to the electrodes. The electrodes sense the electrical signals generated by the patient's heart, muscles, or neural pathways. For example, in ECG, electrical potentials generated in the heart are collected by a system of three, five, or ten electrodes.

Biopotential electrodes are typically single-use and disposable. They rely on a layer of conductive and adhesive gel to both create the electrical connection with the patient's skin and removably affix the electrode to the patient. The adhesive properties of these electrodes deteriorate over the duration of use thereby diminishing the conductive properties as well. This deterioration in conductive properties occurs in two general situations: first by compression and flexion due to the motion of the electrode site if the patient is active, or secondly, when the electrodes have been attached to the patient for an extended period of time, as is found in many long-term hospital and critical care situations.

Therefore, there are clinical advantages to a system that monitors the quality of the connection of electrodes to a patient's skin as, for example, that shown in Simon et al. U.S. Pat. No. 4,577,639. Furthermore, a system that detects a poor connection or disconnected electrode and sends a signal to clinicians to warn them to replace the electrode is also desired. Additionally, or alternatively, the signal could activate a lead-switching network, to select a proper configuration from those electrodes having good connections and maintain a valid measurement with this new configuration, as is also shown in Simon et al.

Most electrode connection quality measurement techniques currently in use measure the resistance or the impedance of the electrode connection. Electrode connection impedance is a composite measurement of many sources of impedance. These include minor contributors such as the impedance of the electrode itself (~100 Ohms), the patient's internal impedance (~100 Ohms), and the impedance of the conductive material in the electrode (~1 KOhm). But the electrode impedance is primarily the electrode-skin interface impedance. This is usually stated to be between 15K$\Omega$ and 1M$\Omega$. See *Med Instr. Application & Design*, Webster, Ed et al. (1998) p. 198.

The epidermal layer of the skin behaves electrically as a parallel RC circuit, and therefore the impedance of the electrode-skin interface is frequency dependent. This is characterized by an epidermal impedance that ranges from approximately 200 KOhms at 1 Hz to 200 Ohms at 1 MHz. (Webster et al.) As the connection between the electrode and/or the skin deteriorates, and should the electrode detach, the impedance of the electrode-skin interface increases.

Electrode connection quality measurement devices are combined with lead switching technology to provide a continuous high quality biopotential measurement. A lead-switching network selects the proper combination of well connected electrodes to produce the desired biopotential signal or signals. An example of such a system is disclosed in Simon '639. An additional example of the electrode connection quality measurement is depicted in FIG. 1 of Marriott U.S. Pat. No. 5,020,541.

Two approaches have developed in the art to determine electrode connection quality. Each approach has its advantages and its limitations. One approach, shown in Simon '639, teaches the injection of a constant DC current to the electrodes. This current will create a DC bias voltage across the electrode-skin interface which is directly proportional to the resistance of the electrode connection. A threshold voltage is set that is indicative of a disconnected electrode and once this threshold is met a "leads off" condition is indicated to the clinician via an alarm or a visual display. Additionally, the lead switching network monitors which electrodes are still well connected and determines the optimal combination of the remaining electrodes to produce a quality ECG signal. This determination is made by referring to a predetermined set of lead switching alternatives or preset optimal combinations based upon which ECG leads are currently in use and which ECG electrode has been disconnected.

The advantage of using a DC current is that no additional frequency component is injected on the patient. Additional frequency components can interfere with the monitoring of other physiological signals, such as EEG and EMG. The disadvantage of the DC method is that the varying DC bias or offset voltage, that provides the measurement of electrode quality, corrupts the biopotential signal and must later be taken out or compensated for to provide an accurate measurement of the biopotential signal. Also, the voltage drop resulting from the DC current may be hard to distinguish from other DC offsets that are present in ECG measurement. Another disadvantage of the DC method is that a DC current will only produce a voltage correlated to the resistance of the electrode connection. The electrode, however, is not purely resistive and to provide an accurate analysis of the electrode connection quality other frequency dependent properties, such as capacitance, must also be taken into account.

The approach of utilizing an AC signal for the on-off determination of electrode connection is taught by Morgan in U.S. Pat. No. 4,619,265. This approach is similar in method to the DC approach, except that an AC signal is injected and the impedance of the electrode is measured instead of the resistance. The Marriott '541 patent, noted above, depicts such use of an AC signal for an ECG electrode quality determination system. Marriott '541 discloses the injection of two out of phase AC carrier signals. One signal is sent to a reference lead and the other signal is sent to a plurality of collection leads. The different combinations of ECG electrode signals are supplied to differential amplifiers wherein the amplitudes of two AC carrier signals are compared to determine a differential voltage measurement that corresponds to the impedance of the electrode interface for a given ECG lead. This measurement can be analyzed by downstream components to detect and indicate electrode connection quality or a leads off condition.

The advantage of utilizing AC signals is that the impedance of the electrode connection can be measured to provide a more accurate picture of the entire connection over that provided by the DC method that measures only resistance. The disadvantage of utilizing AC signals is that they inject a frequency component onto the patient. This can interfere with the concurrent measurement of other physiological parameters of the patient by other pieces of monitoring equipment, especially equipment such as EEG and EMG equipment.

While the foregoing describes the collection of biopotential signals from a patient, the electrical quality of a patient-electrode interface is also important when electrical energy is applied to a patient, as by a defibrillator.

SUMMARY OF THE INVENTION

The present invention provides an apparatus for the improved detection and measurement of electrode connection or interface quality is provided. The electrode interface quality so determined may be displayed in a useful manner and used to carry out electrode lead switching.

The electrode connection quality detection apparatus employs a carrier signal source, a signal collection preamplifier, a digital signal processor, and a lead switching network. The carrier signal source injects both AC and DC carrier signals onto the patient. These signals are collected along, with the biopotential signals from biopotential electrodes applied to the skin of the patient and supplied to differential amplifiers in the preamplifier. The analog signals are filtered and digitized in the digital signal processor. The desired biopotential signals are extracted and can be displayed or otherwise used for diagnostic purposes.

The injected carrier signal data is sent to a microprocessor in the digital signal processor which determines the electrode connection quality. The electrode connection quality may also be displayed. Also, if the microprocessor detects a failed or disconnected electrode, a signal is sent to the lead switching network which in turn selects a viable configuration of electrodes to enable the collection of the biopotential signals to continue.

The present invention combines the use of both AC and DC impedance measurement techniques simultaneously to provide a graduated measurement of electrode connection quality. This graduated measurement can be displayed in real time to provide an early warning before lead failure occurs.

In a further embodiment of the present invention the AC measurement component may be turned off to reduce the adverse effects of the electrode connection quality measurement on various other pieces of biopotential monitoring equipment due to interference. This allows the present invention to operate with input portions in a low emission DC "quiet" mode so that the additional frequency component does not interfere with the measuring of other biopotentials by other monitoring equipment.

The AC carrier signal may comprise a single AC signal or may comprise two signals that are of equal amplitude but are out of phase and injected onto different electrodes.

The invention may also find use in automatic portable defibrillators. Defibrillation requires the proper low impedance connection of the defibrillation electrodes to the patient. An improved technique for measurement of electrode connection quality would potentially provide increased safety for the caregiver or operator and clinical efficacy benefits to the patient.

DETAILED DESCRIPTION OF THE INVENTION

Figure 1:
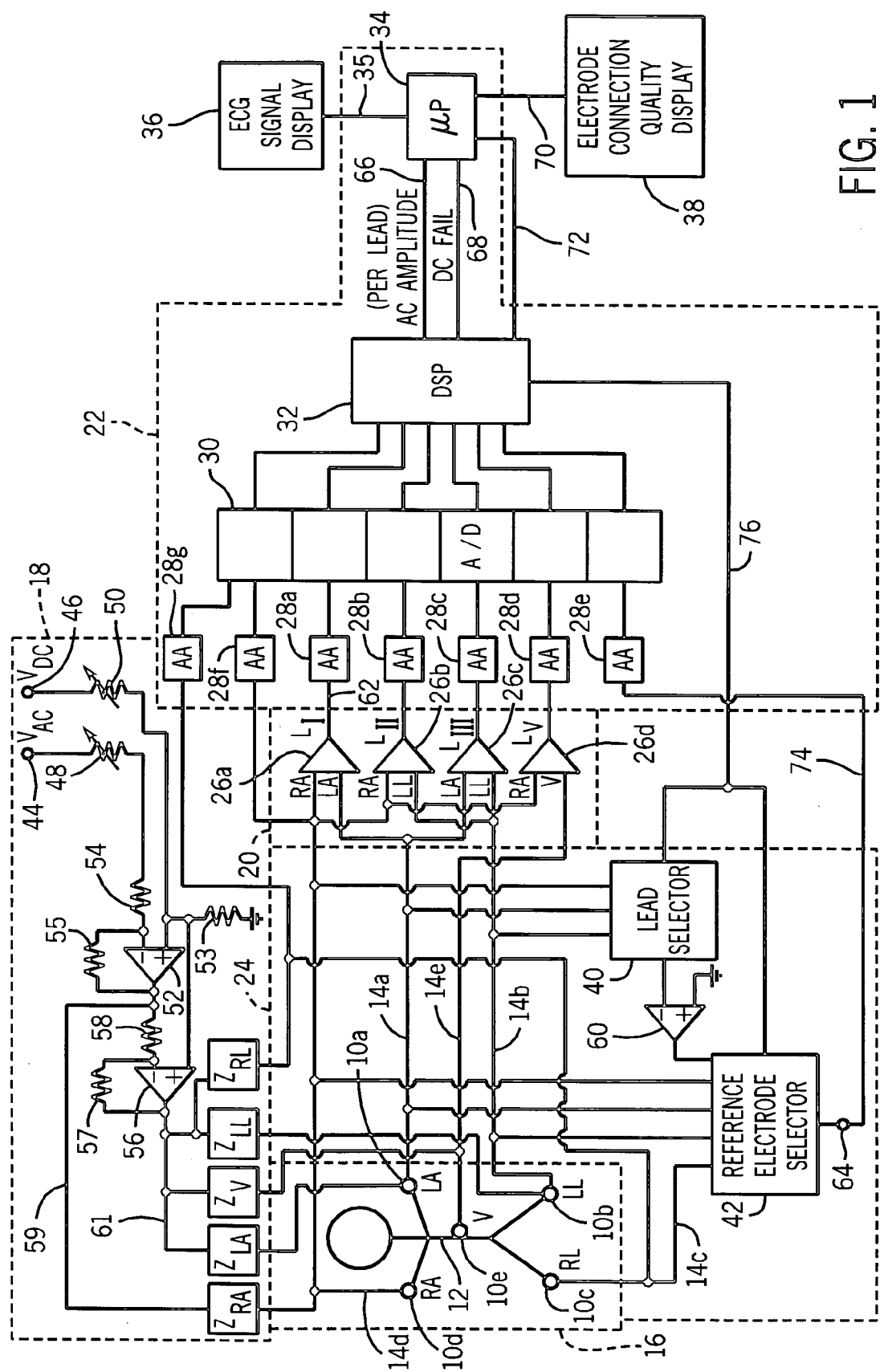
FIG. 1 is a schematic diagram of an embodiment of a dual mode AC/DC impedance measurement apparatus for biopotential electrode interface connection quality of the present invention.

FIG. 1 is a schematic diagram of a dual mode AC/DC impedance measurement apparatus for assessment of electrode interface connection quality. The apparatus is exemplarily shown in an electrocardiographic environment.

Referring now to FIG. 1, electrodes 10a-e are shown applied to the skin of patient 12. FIG. 1 shows the conventional designation for such electrodes, such as LA (left arm), LL (left leg), V (chest), etc. Electrodes 10 are connected to corresponding conductors 14a-e of a patient connection system 16 that connects the electrodes to an electrical device, such as an electrocardiograph or cardiac monitor. Selected pairs of conductors 14 form electrocardiographic leads. While one chest electrode is shown in FIG. 1 for illustrative purposes, conventional systems may utilize a plurality of chest electrodes applied to the patient.

The impedance measurement apparatus comprises the operational blocks of a carrier signal source 18, an ECG preamplifier circuit 20, signal processor 22, and a lead switching network 24. The carrier signal source 18 operates to provide AC and DC carrier signals to the electrodes applied to patient 12 through the conductors 14 of patient connection system 16. The ECG preamplifier circuit collects the ECG signals and the carrier signal for each desired ECG lead using amplifiers such as 26a, 26b, 26c, and 26d which signals are then sent to signal processor 22. The signal processor comprises a plurality of anti aliasing filters 28a-28g, a single multiplexed A/D converter 30, a digital signal processor (DSP) 32 and a microprocessor 34. The signal processor 22 serves to convert the signals from the preamplifier circuit 20 to digital signals so that the DSP 32 can extract the AC carrier, DC carrier, and ECG signals. These signals are sent to microprocessor 34 and used to determine electrode connection quality, which is then displayed on display 38.

Upon detection of a leads off condition, microprocessor 34 sends a signal via digital signal processor 32 and conductors 72 and 76 to lead switching network 24 comprising lead selector 40 and reference electrode selector 42 whereby lead switching network 24 selects a functional set of ECG leads and a reference electrode to maintain the collection of the ECG signal by the biopotential electrodes.

Carrier signal source 18 is connectable to an AC signal source at 44 and a DC signal source at 46. The AC signal that is supplied to carrier signal source 18 is typically in a range of 240 Hz to 800 Hz. The peak magnitude of the AC signal and DC signal from the signal sources is controlled by variable resistors 48 and 50 respectively. The AC signal is sent to the inverting input of operational amplifier 52 through resistor 54. The DC signal is sent through a voltage divider formed by resistors 50 and 53 to the non-inverting inputs of operational amplifiers 52 and 56. The output of amplifier 52 is connected to the inverting input of operational amplifier 56 through resistor 58. Operational amplifiers are implemented in a conventional manner with feedback being provided via resistors 55 and 57 respectively. This combination of operational amplifiers produces two AC signals with a positive DC offset that are 180° out of phase with each other. One signal is provided in conductor 59. The other signal is provided in conductor 61.

The output of amplifier 52 is connected to the patient at the patient's right arm (RA) electrode 10d via conductor 59. This signal sees an impedance shown diagrammatically in FIG. 1 as $Z_{RA}$ which is a combination of the lead wire 14d impedance, the electrode-to-skin impedance, the patient's internal impedance, the impedance of electrode 10d, and the impedance of the conductive component of the electrode. The output of amplifier 56 is connected in the same manner via conductor 61 to the patient's left arm (LA) at electrode 10a, chest (V) at electrode 10e, left leg (LL) at electrode 10b, and right leg (RL) at electrode 10c. This signal sees impedances that are similar to $Z_{RA}$, which are designated as $Z_{LA}$, $Z_V$, $Z_{LL}$, and $Z_{RL}$. It is understood that an alternative design may be implemented with the output of amplifier 52 connected to electrodes 10a, 10b, 10c, and 10e while the output of amplifier 56 is connected to electrode 10d.

In preamplifier circuit 20, the ECG signals combined with the injected carrier signals are collected by amplifiers 26a, 26b, 26c, and 26d to provide the necessary combination of signals from the electrodes to provide ECG lead LI, lead LII, lead LIII and lead LV signals at the outputs of this preamplifier circuit. The lead LI ECG signal is produced by signals collected from the right arm electrode 10d and the left arm electrode 10a, the lead LII ECG signal is produced from the signals from the right arm electrode 10d and left leg electrode 10b, the LIII ECG signal is produced from the signals from the left arm electrode 10a and left leg electrode 10b, and the lead LV ECG signal is produced from the ECG signal from right arm electrode 10d and the ECG signal from chest electrode 10e.

The electrode and lead portion of the circuitry shown in FIG. 1 also include driver 60 which is a common-mode driver amplifier with its input connected to lead selector 40 and its output connected to the appropriate reference electrode by reference electrode selector 42 for common mode interference or noise reduction.

The injected AC carrier signal supplied to right arm electrode 10d is 180° out of phase with the AC carrier signal that is supplied to electrodes 10a, 10e, and 10b so that when the different combinations of electrode signals are processed by preamplifier circuit 20, there is always a differential AC signal for amplifiers 26a, 26b, 26c, and 26d during multilead operation. This produces the desired ECG lead signals along with the AC carrier amplitude and DC signal level offsets resulting from the injected carrier signals and the impedances of each of the electrode connections. These ECG lead signals from ECG preamplifier 20 are sent to the signal processor 22.

The ECG LI, LII, LIII and LV lead signals from the ECG preamplifier 20 are substantially similar in nature so the further signal processing of these signals is described, in detail, with respect to the ECG LI lead signal from amplifier 26a in conductor 62. The signal in conductor 62 is sent to an anti-aliasing filter 28a. Additionally, a reference signal from the reference electrode selected by reference electrode selector 42 and indicated at 64, is sent to anti-aliasing filter 28e. A suitable anti-aliasing filter would be a 2 pole low pass filter with a corner frequency at 360 Hz. These signals from the anti-aliasing filters are sent to a multiplexed A/D converter 30 which samples the signals and digitizes them to be processed further by digital signal processor 32. Digital signal processor 32 employs appropriate filters to extract the AC carrier amplitude, DC signal level, and ECG lead LI signal information. These signals are provided to microprocessor 34 for further analysis. Additionally, microprocessor 34 provides the ECG lead LI signal data through conductor 35 for display on ECG signal display 36.

Digital signal processor 32 provides AC carrier amplitude 66 and DC signal level 68 to microprocessor 34 which uses these signals in conjunction with an appropriate algorithm to generate a quantification of the electrode connection quality for the ECG LI lead. The amplitude of the AC signal in conductor 66 is indicative of the impedance of the electrode connection. The level of the DC signal is used in determining connection or disconnection (failure) of the electrode to the skin. For this reason, this aspect of the signal analysis is more binary in nature.

The measurement and quantification of electrode interface quality is aided in the present invention because, since this system for measuring electrode interface connection quality utilizes both AC and DC carrier signals, a better estimate of electrode quality is possible, including a gradation system categorically rating the electrode connection quality. This measurement of electrode connection quality may be sent to electrode connection quality display 38 in conductor 70 so that a real time measurement of electrode connection quality is readily available to the attending clinician. Display 38 may display the value as a categorical gradation of the electrode connection quality. For example, the categorical gradation may include the levels of excellent, good, fair and poor. This visual indication of the electrode connection quality, will enable the clinician to observe any deterioration of electrode connection quality over time. This presentation of electrode connection quality could provide the beneficial effect of providing an advance warning of electrode connection insufficiency which, if good estimates of electrode connection quality can be trended, could translate into 30 minutes to 2 hours of advance warning before a "leads off" condition occurs.

Upon detection of a "leads off" or disconnection condition, as determined through analysis of the DC carrier signal, microprocessor 34 utilizes an electrode selection algorithm to select an appropriate combination of the remaining electrodes to maintain proper ECG signal collection. This selection data is sent via conductor 72 to digital signal processor 32, which in turn sends it to lead switching network 24 via conductor 76. Reference electrode selector 42 also receives the signal in conductor 76 and appropriately switches the reference electrode in the system. Alternatively, the electrode "leads off" detection may be performed by digital signal processor 32 and the electrode selection performed by microprocessor 34. The AC and DC signal conditions appearing at the reference electrode 64 are sent along conductor 74 to anti-aliasing filter 28e and on to A/D converter 30 to aid in signal analysis by digital signal processor 32. The lead switching signal sent from microprocessor 34 along conductors 72 and 76 is also received by lead selector 40. Lead selector 40 selects the active lead to be used by driver 60 in conjunction with the selected reference electrode for common mode noise reduction in the collection of ECG signal data.

Figure 2:
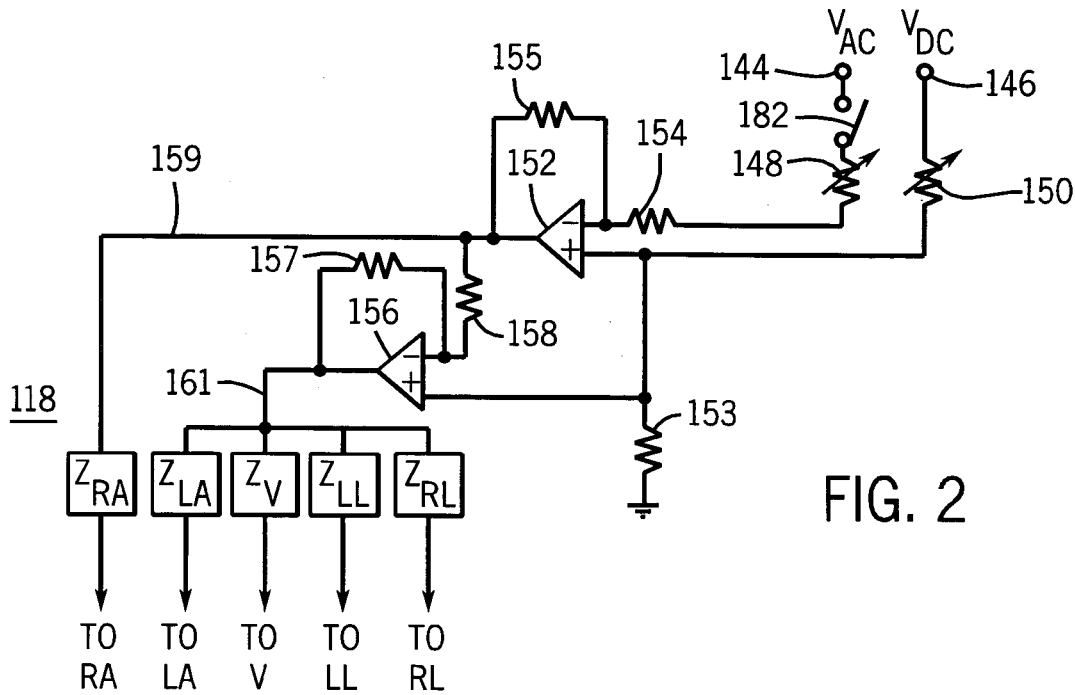
FIG. 2 is a partial schematic diagram of a portion of the apparatus showing an alternative embodiment.

FIG. 2 is a partial schematic diagram of an alternative embodiment of the dual mode AC/DC impedance measuring apparatus of the present invention. Specifically, in FIG. 2, the carrier signal source 118 includes the same basic components as depicted in FIG. 1, and have been labeled with analogous numbers. However, a switch 182 is included between the AC voltage source 144 and the variable resistor 148. Switch 182 allows the clinician to turn off the injected AC signal from source 144 to enable the apparatus to operate in a low emissions DC "quiet" mode. As noted above, an injected AC signal can interfere with the measurement of other concurrently monitored biopotentials such as EEG and EMG. Giving a clinician the ability to deactivate the injected AC signal, when desired, will eliminate or lessen interference with the other concurrently monitored biopotentials while still providing a reliable assessment of electrode connection based on the injected DC signal.

Figure 3:
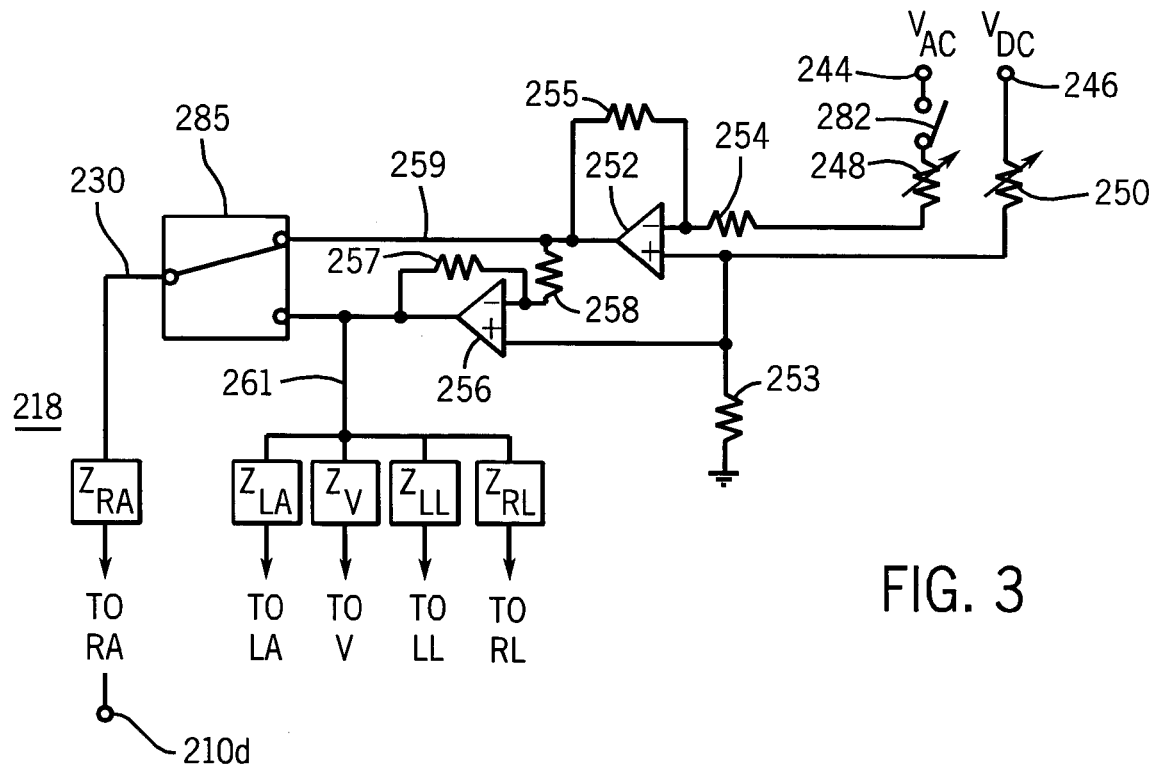
FIG. 3 is a partial schematic diagram of a portion of the apparatus showing a further embodiment of the present invention.

FIG. 3 is a partial schematic diagram of a further embodiment of the dual mode AC/DC impedance measuring apparatus. Specifically, in FIG. 3, the carrier signal source 218 is shown as substantially the same as the carrier signal source shown in FIG. 2, and has been labeled with analogous numbers. However, a switch 285 is disposed between operational amplifier 256, operational amplifier 252 and conductor 230 which provides the injected carrier signal to the RA electrode 210*d*. Switch 185, which may comprise a 2 to 1 multiplexer, allows the phase of the AC carrier signal injected to the RA electrode 210*d* to be switched, thus allowing the signal source for the $Z_{RA}$ impedance to be connected as shown in FIGS. 1 and 2 or to be driven from the same carrier signal source as the other ECG electrodes. This allows the AC carrier component supplied to right arm electrode RA to be 180° out of phase with the others for a normal multi-lead operating mode or in phase with the others when single lead vector operation is required, for example, when the RL electrode connection has failed or is not present and data is collected using only the RA, LA, and LL electrodes. This operation mode is also applicable in other single lead monitoring situations, such as when the RA and RL electrodes are connected and either the LA or LL lead has become disconnected.

It is recognized that other equivalents, alternatives, and modifications in addition to those expressly stated, are possible including the replacement of components described herein with their electronic or software counterparts. Various alternatives and embodiments are contemplated as being within the scope of the following claims particularly pointing out and distinctly claiming the subject matter regarded as the invention.

What is claimed is:

1. Apparatus for assessing the electrical properties of an interface between a patient and electrodes applied to the patient, said apparatus comprising:

a carrier signal source couplable to the electrodes, said carrier signal source receiving DC energization and AC energization and outputting two carrier signals comprising an AC signal with a DC offset, the two carrier signals being out of phase with each other by a preselected amount, one of said carrier signals being suppliable to a selected one of said electrodes, the other of said carrier signals being suppliable to others of said electrodes;

amplifier means comprising at least one amplifier each having a pair of inputs, one of said inputs being couplable to the selected one of the electrodes, the other input being couplable to another of said electrodes, said amplifier producing an output lead signal in which AC and DC offset characteristics result from the electrical properties of the patient interfaces at the electrodes; and signal processing means coupled to said amplifier means and receiving said output lead signal of said amplifier, said signal processing means having means for obtaining and providing a first signal comprising the AC signal characteristics of the output lead signal and for providing a second signal comprising the DC characteristics in the output lead signal, said signal processing means having means employing said first signal to provide a first output indicative of the quality of an interface between the electrodes and the patient and said second signal to provide a second output indicative of the status of the connection between the electrodes and the patient.

2. The apparatus according to claim 1 wherein said carrier signal source is further defined as providing two carrier signals phase shifted by 180° from each other.

3. The apparatus according to claim 1 wherein said carrier signal source comprises a pair of cascaded amplifiers.

4. The apparatus according to claim 3 wherein said amplifiers receive AC energization to inverting input terminals and DC energization to non-inverting input terminals.

5. The apparatus according to claim 1 wherein said carrier signal source provides carrier signals incorporating AC energization having a frequency between about 240-800 Hz.

6. The apparatus according to claim 1 wherein said amplifier means includes a plurality of amplifiers.

7. The apparatus according to claim 1 wherein said signal processing means further provides signals containing physiological data from the patient.

8. The apparatus according to claim 7 wherein said signal processing means provides signals containing electrocardiographic data from the patient.

9. The apparatus according to claim 1 wherein said signal processing means further includes filter means for obtaining and providing said first and second signals, digital signal processing means for digitizing said first and second signals and wherein said means employing said first and second signals comprises a microprocessor.

10. The apparatus according to claim 1 wherein said means providing said first and second signals comprises a signal separator and a digital signal processor and wherein said means employing said first and second signals comprises a microprocessor.

11. The apparatus according to claim 1 wherein said means providing said first and second signals comprises a signal separator/digital signal processor for obtaining and providing said first and second signals and wherein said means employing said first and second signals comprises a microprocessor.

12. The apparatus according to claim 1 further comprising a display means coupled to said means employing said first and second signals for displaying said first and second outputs.

13. The apparatus according to claim 12 wherein said display means displays gradation of electrode interface quality and a binary indication of electrode connection display means.

14. The apparatus according to claim 13 wherein said display means displays an output indicating changes in electrode interface quality with respect to time to indicate potential for electrode connection failure.

15. The apparatus according to claim 1 wherein said carrier signal source includes means for selectively removing the AC energization from said carrier signals.

16. Apparatus for assessing the electrical properties of an interface between a patient and electrodes applied to the patient, said apparatus comprising:

a carrier signal source couplable to the electrodes, said carrier signal source receiving DC energization and AC energization and outputting two carrier signals comprising an AC signal with a DC offset, the two carrier signals being out of phase with each other by a preselected amount, one of said carrier signals being suppliable to a selected one of said electrodes, the other of said carrier signals being suppliable to others of said carrier signals being suppliable to others of said electrodes wherein the carrier signal source includes means for selectively removing AC energization from said carrier signals;

amplifier means comprising at least one amplifier each having a pair of inputs, one of said inputs being couplable to the selected one of the electrodes, the other input being couplable to another of said electrodes, said amplifier producing an output lead signal which AC and DC offset characteristics result from the electrical properties of the patient interfaces at the electrodes; and signal processing means coupled to said amplifier means and receiving said output lead signal of said amplifier, said signal processing means having means for obtaining and providing a first signal comprising the AC signal characteristics of the output lead signal and for providing a second signal comprising the DC characteristics in the output lead signal, said signal processing means having means employing said first and second signals to provide an output indicative of the electrical properties of an interface between a patient and electrodes applied to the patient.

17. Apparatus for assessing the electrical properties of interfaces between a patient and electrodes applied to the patient, said apparatus comprising:

a carrier signal source couplable to the electrodes the carrier signal source receiving DC energization and AC energization and outputting a carrier signal including DC energization;

the carrier signal being applied to at least one of the electrodes;

a switch coupled to the carrier signal source and to the AC energization, the switch being operable to selectively include AC energization in the carrier signal;

a signal processor in communication with the electrodes and receiving from the electrodes a signal in which DC offset characteristics and selectively AC offset characteristics result from the electrical properties of the interfaces between the patient and the electrodes, the signal processor providing a first signal comprising the AC offset characteristics and a second signal comprising the DC offset characteristics, the signal processor employing the first signal to provide a first output indicative of the quality of the interfaces between the electrodes and the patient and employing the second signal to provide a second output indicative of the status of the correction between the electrodes and the patient.

18. The apparatus according to claim 17 further comprising a visual display coupled to the processor, the display displaying the first and second outputs.

19. The apparatus according to claim 18 wherein the display of the first output is a categorical gradation of electrode interface quality and the display of the second output is a binary indication of electrode connection.

20. The apparatus according to claim 18 wherein the first output indicates changes in electrode interface quality with respect to time.

* * * * *